(12) United States Patent
Lawman et al.

(10) Patent No.: US 7,015,034 B2
(45) Date of Patent: Mar. 21, 2006

(54) MATERIALS AND PROCEDURES FOR THE PURIFICATION OF CELLS

(75) Inventors: Michael J. P. Lawman, Chipley, FL (US); Patricia Lawman, Chipley, FL (US)

(73) Assignee: Morphogenesis, Inc., Chipley, FL (US)

( * ) Notice: Subject to any disclaimer, the term of this patent is extended or adjusted under 35 U.S.C. 154(b) by 0 days.

(21) Appl. No.: 09/981,639

(22) Filed: Oct. 17, 2001

(65) Prior Publication Data

US 2002/0115113 A1   Aug. 22, 2002

Related U.S. Application Data

(63) Continuation of application No. 09/437,509, filed on Nov. 10, 1999, now abandoned, which is a continuation of application No. 08/965,949, filed on Nov. 7, 1997, now abandoned.

(60) Provisional application No. 60/030,725, filed on Nov. 8, 1996.

(51) Int. Cl.
*C12N 5/00* (2006.01)
*C12Q 1/24* (2006.01)

(52) U.S. Cl. .................. 435/325; 204/403.1; 435/2; 435/7.1; 435/7.21; 435/7.24; 435/7.5; 435/30; 435/287.2; 435/372; 436/528; 436/535; 436/806

(58) Field of Classification Search .............. 435/2, 435/7.1, 7.21, 7.24, 7.5, 30, 287.2, 372, 325; 436/528, 535, 806; 204/403.1
See application file for complete search history.

(56) References Cited

U.S. PATENT DOCUMENTS

| | | | |
|---|---|---|---|
| 4,839,017 A | 6/1989 | Taniguchi | 204/403 |
| 4,916,075 A * | 4/1990 | Malmros et al. | 435/291 |
| 5,059,694 A | 10/1991 | Delabouglise | 548/518 |
| 5,132,049 A | 7/1992 | Garreau | 252/500 |
| 5,149,826 A | 9/1992 | Delabouglise | 548/518 |
| 5,156,810 A * | 10/1992 | Ribi | 422/82.01 |
| 5,256,271 A | 10/1993 | Ikariyama et al. | 204/403 |
| 5,310,469 A | 5/1994 | Cunningham et al. | 204/403 |
| 5,403,451 A * | 4/1995 | Riviello et al. | 204/153.1 |
| 5,440,025 A | 8/1995 | Marx et al. | 536/25.4 |
| 5,491,097 A | 2/1996 | Ribi et al. | 436/5.8 |
| 5,843,741 A * | 12/1998 | Wong et al. | 435/173.8 |
| 6,096,825 A * | 8/2000 | Garnier | 525/54.1 |
| 6,184,030 B1 | 2/2001 | Katoot et al. | 435/287.2 |

FOREIGN PATENT DOCUMENTS

| | | |
|---|---|---|
| GB | 2276724 | * 10/1994 |
| WO | 8903876 | 5/1989 |
| WO | 8911648 | 11/1989 |
| WO | 9402016 | 2/1994 |
| WO | 9529199 | 11/1995 |
| WO | 9604340 | 2/1996 |

OTHER PUBLICATIONS

Cruse et al, Illustrated Dictionary of Immunology, CRC Press, Inc., p. 110, 1994.*
Englebienne, P., M. Welland (1996) "Water-soluble conductive polymer homogenous immunoassay (SOPHIA), A novel immunoassay capable of automation" *Journal of Immunological Methods* 191:159-170.

(Continued)

*Primary Examiner*—David Saunders
(74) *Attorney, Agent, or Firm*—Saliwanchik, Lloyd & Saliwanchik (57) ABSTRACT

The subject invention provides new materials and methods for the efficient isolation and purification of stem cells. Specifically, conductive immunopolymers with stem cell specific antibodies can be used to remove stem cells from biological fluids.

22 Claims, 5 Drawing Sheets

FIG. 1

OTHER PUBLICATIONS

Loh, Ih-Houng, R. Moody, J.C. Huang (1990) "Electrically Conductive Membranes: Synthesis and Applications" *Journal of Membrane Science* 50:31-49.

Alva, K.S. et al. (1996) "Novel immobilization techniques in the fabrication of efficient electrochemical biosensors" *S.P.I.E.* 2716:152-163.

Bender, J.G. et al. (1991) "Identification and Comparison of CD34-Positive Cell and Their Subpopulations From Normal Peripheral Blood and Bone Marrow Using Multicolor Flow Cytometry" *Blood* 77(12):2591-2596.

Berenson, R.J. et al. (1991) "Engraftment After Infusion of CD34+ Marrow Cells in Patients With Breast Cancer of Neuroblastoma" *Blood* 77(8):1717-1722.

Wong et al. (1994) "Electrically Conducting Polymers Can Noninvasively Control the Shape and Growth Mammalian Cells" *PNAS* 91:3201-3204.

Prezyna et al. (1991) "Interaction of Cationic Polypeptides with Electroactive Polypyrrole/Poly (Styrenesulfonate) and Poly (N-methylpyrrole)/Poly(Styrene sulfonate) Films" *Macromolecules* 24:5283-5287.

Smith et al. (1991) "Investigation of the Relationship Between Conductivity and Protein-Binding Properties of Polypyrrole" *J. Appl. Polym. Sci.* 43:399-403.

de Wynter, E.A. et al. (1995)"Comparison of Purity and Enrichment of CD34+ Cells from Bone Marrow, Umbilical Cord and Peripheral Blood (Primed for Apheresis) Using Five Separation Systems" *Stem Cells* 13-524-532.

Zeheb, R., V. Change, G.A. Orr (1983) "An Analytical Method for the Selective Retrieval of Iminobloin-Derivatized Plasma Membrane Proteins" *Analytical Biochemistry* 129:156-161.

* cited by examiner

MATERIALS AND PROCEDURES FOR THE PURIFICATION OF CELLS

CROSS-REFERENCE TO RELATED APPLICATIONS

This application is a continuation of application U.S. Ser. No. 09/437,509, filed Nov. 10, 1999, now abandoned, which is a continuation of application U.S. Ser. No. 08/965,949, filed Nov. 7, 1997, now abandoned, which claims the benefit of provisional application U.S. Ser. No. 60/030,725, filed Nov. 8, 1996.

BACKGROUND OF THE INVENTION

Mammalian blood cells provide for an extraordinarily diverse range of activities. Hematopoietic stem cells are defined as those cells that are capable of both self-renewal and differentiation into the two principle precursor components—the myeloid and lymphoid lines. Such stem cells are said to be "totipotent." Stem cells that are less general but that can still differentiate into several lines are called "pluripotent." Further differentiation then occurs among the precursor cells to produce the monocyte, eosinophil, neutrophil, basophil, megakaryocytes, and erythroid lineages from the myeloid line, and T cells, B cells, and NK cells from the lymphoid line. Hematopoietic stem cells reside primarily in the bone marrow.

One of the first breakthroughs into stem cell isolation and identification came in the late 1980's. In U.S. Pat. No. 4,714,680, Civin described pluripotent lympho-hematopoietic cells that were substantially free of mature lymphoid and myeloid cells. Civin also described an antigen, MY-10, and a monoclonal antibody thereto, which was present on those cells. Those cells made up about 1% of all cells in normal adult bone marrow, and generally comprised a mixture of totipotent, and pluripotent stem cells and lineage committed precursor cells with the latter cells predominating. Since that time, MY-10 has been classified by the International Workshop on Human Leukocyte Antigens as falling with the cluster designated as "CD34." Anti-CD34 monoclonal antibodies are now commercially available from a number of sources including, for example, Becton Dickinson Immunocytometry Systems ("BDIS").

Other investigators have attempted to subset $CD34^+$ cells from both peripheral blood and bone marrow. Bender et al., *Blood* 77:2591–2596 (June 1991), used four color flow cytometry with combinations of monoclonal antibodies (i.e., anti-CD34, anti-CD33, anti-CD45, anti-CD19, anti-CD7, anti-CD10, anti-CD3, anti-CD20, anti-CD14, anti-CD11b and anti-HLA-DR), to identify and isolate $CD34^+$ hematopoietic progenitor cells.

There is a strong interest in identifying and isolating human hematopoietic stem cells. However, the stem cell population constitutes only a small percentage of the total number of leukocytes in bone marrow. In view of the small proportion of the total number of cells in the bone marrow which are stem cells, the uncertainty of the markers associated with the stem cell as distinct from more differentiated cells, and the general inability to biologically assay for human stem cells, the identification and purification of stem cells has been difficult.

Having a procedure for the efficient isolation of stem cells would allow for identification of growth factors associated with, for example, (1) the early steps of dedication of the stem cell to a particular lineage; (2) the prevention of such dedication; and (3) the negative control of stem cell proliferation. Readily available stem cells would also be extremely useful in bone marrow transplantation, as well as transplantation of other organs in association with the transplantation of bone marrow. Also, stem cells are important targets for gene therapy, where the inserted genes promote the health of the individual into whom the stem cells are transplanted. In addition, the ability to isolate stem cells may serve in the treatment of lymphomas and leukemia, as well as other neoplastic conditions. The identification and isolation of the most primitive population of hematopoietic stem cells would be highly advantageous in situations where reinfusion of only a small number of long-term repopulating cells was desired. For example, this would be the case when purging bone marrow or peripheral blood stem cells of contaminating tumor cells, or where genetic manipulation of the stem cells was the objective.

The separation of a particular mammalian cell population from a mixture of cell populations is quite different from the separation of chemical species such as proteins from a solution. Most mammalian cells are on the order of 8 to 20 microns ($\mu$) in diameter. In contrast, the proteins and other chemical species are significantly smaller, i.e., on the order of 1000-fold or more. In addition, another factor unique to the separation of mammalian cells is the need to preserve cell viability.

In contrast to yeast cells, which are relatively insensitive to changes in osmolarity, pH and shear, higher order mammalian cells are much more sensitive to shear forces-exerted during purification, pH osmolarity, and the chemical composition of the reagents used. Therefore, the steps comprising the method and all reagents used must be non-toxic to the cells.

Separation of mixtures of chemicals, biomolecules and cell types is often effected by immunoaffinity chromatography. Packed beds, such as those used in column chromatography, are often used in affinity separation. However, problems such as non-specific trapping or filtration of cells and clogging make the use of a packed bed undesirable for cell separation.

One device that has been developed for reducing the pressure drop across a column of particles is the fluidized bed. A fluidized bed consists of solid particles and a gas or liquid which is passed upwardly through the particle bed with velocity sufficient to fluidize the bed. The fluidization of the bed provides more surface contact between the particle and the fluid passing through the bed. One disadvantage associated with fluidized beds is the radial and axial movement of the particles which result in significant intermixing of the particles.

A number of other methods have been developed for fractionating heterogeneous mixtures of cells into the various compartments. These methods are based on the size and density of the cells, specific binding properties that they possess, and their expression of surface antigens. The method chosen usually depends on the degree of purity required, the intended use of the selected cells, and the abundance of the cells of interest.

Density gradient centrifugation, velocity sedimentation, and counterflow centrifugal elutriation are methods currently used to separate cells based on their physical properties such as size and density. While these methods work well as pre-enrichment steps, none are accurate and/or specific enough to yield pure populations of stem cells.

Flow cytometry is extremely sensitive because it looks at each cell individually. It can distinguish multiple markers, their relative level of expression, the size and granularity of each cell, and can sort out specific cells into a waiting tube.

However, the equipment is highly sophisticated, the processing is relatively slow, and it is difficult to sterilize the instrument between samples.

By immobilizing the antibody on a solid phase, several methods have been used to process larger cell numbers in a relatively short time while still exploiting the specificity of the antigen/antibody interaction. Panning is an effective three-step technique for cell selection. First, mononuclear cells are separated from bone marrow, peripheral, or cord blood by density gradient centrifugation, negatively panned for soybean agglutinin binding, and positively panned with an anti-CD34 antibody-coated flask. The selected cells are released by mechanical agitation. The major problems with this method are the multiplicity of steps, subsequent low yields and the surface area required to give clinically useful stem cell numbers.

Another method along these lines uses magnetic beads as a solid support. Mononuclear cells are incubated with anti-CD34 antibody and bound to magnetic beads coated with sheep anti-mouse antibodies. The CD34+ cells are pulled to the side of the tube by applying a magnet. Historically, it has been difficult to dislodge the beads from the cells without harming the cells and perhaps of greater concern is that incomplete removal of the beads prior to reinfusion may be harmful to the patient.

One clinical technique is cell separation by avidin-biotin column chromatography as developed by Berenson et al. White blood cells incubated with a biotinylated anti-CD34 antibody are applied to a column containing avidin-coated polyacrylamide or agarose beads. After washing, the bound $CD34^+$ cells are stripped from the bed by mechanical agitation. Theoretically, the mechanical release breaks the link at its weakest point, the antigen/antibody, and leaves the CD34 antigen intact on the cell surface. This is proposed because of the high affinity between biotin and avidin. Cells selected from bone marrow, peripheral blood, and cord blood by this method have been allogenically (unrelated donor) or autologously (self) transplanted into more than 200 patients worldwide to treat breast cancer, neuroblastoma, non-Hodgkin's lymphoma, and chronic myelogenous leukemia.

There are a number of innate problems facing any rare cell separation system. For instance, large surfaces tend to bind cells nonspecifically, thus decreasing specificity. Whereas low specificity is easy to overcome in systems where large numbers of the desired cells are available, it becomes a critical factor in separating stem cells since they are in such low abundance and in a heterogeneous cell background. Detachment is also a problematic stage in separation procedures. Detachment methods currently employed include the use of enzymes that chemically clip the cells from the solid phase, mechanical methods which tear them off, and polyclonal antibodies which compete them off.

A highly purified population of stem cells is necessary for a variety of in vitro experiments and in vivo indications. For instance, a purified population of stem cells will allow for identification of growth factors associated with their self-regeneration. In addition, there may be as yet undiscovered growth factors associated (1) with the early steps of dedication of the stem cell to a particular lineage; (2) the prevention of such dedication; and (3) the negative control of stem cell proliferation.

A comparison between current cell selection methods has proven that the use of antibodies to target specific cell populations consistently results in higher specificity and recovery when compared to non-antibody based methods. However, the current methods cannot produce pure cell populations (purity $\leq 70\%$) and cannot recover more than 65% of the target cells (de Wynter et al., 1995). All current methods require the sample to be collected, often frozen and transferred to the laboratory for cell selection/depletion. None of the existing devices has the capacity to perform "in line" cell selection, that is, to directly select cells from normal peripheral blood as it is being drawn from a donor. Such possibility would make stem cell donation as simple as blood donation and would have enormous implications in the field of stem cell transplantation. It would tremendously increase the number of potential donors and expand the histocompatibility repertoire of stem cells available for transplantation, probably making the concept of stem cell banks a reality. The subject invention provides an efficient system for stem cell purification.

BRIEF SUMMARY OF THE INVENTION

The subject invention pertains to materials and methods for target molecule and cell separation and, in particular, stem cell separation, using a polymer system. In a preferred embodiment the polymer is a conductive polymer. In one embodiment, an immunopolymer useful according to the subject invention comprises a conductive solid matrix wherein antibodies are entrapped. Preferably, these antibodies are monoclonal antibodies. The polymer with the antibodies is then contacted with a composition containing stem cells. The stem cells become associated with the antibodies within the polymer while the rest of the composition, including irrelevant cells, and other material passes through the system. The stem cells can then be released from the polymer by application of an appropriate current.

The use of an electric current to induce the release of bound cells from the immunopolymer surface provides a reliable, reproducible, and gentle method to harvest unaltered selected cells. Also, since this technique permits the monitoring of cell binding to the solid matrix during the selection process, it is possible to obtain feedback information on the number of selected cells at any time.

DETAILED DISCLOSURE OF THE INVENTION

The methods of the subject invention involve the use of molecules such as a protein, antibody or nucleic acid capable of binding to a target moiety. Exemplified herein is the use of cell-specific antibodies combined with a polymer. In accordance with the teachings of the subject invention, the antibodies are trapped inside the polymer matrix as it is formed without loss of their binding functions. A complex mixture of cells and other materials can then be passed over the polymer-antibody complex, unbound cells and other materials are removed by washing, and the cells that are trapped by the antibody can be released into a collection tube by reversing the conditions of polymer formation. Specifically, an electric current used to make a polymer can be reversed thus resulting in the release of the desired cells.

The major advantages of the system of the subject invention include the stability of the polymer-antibody complex; the polymer itself does not bind unwanted cells like the beads and panning surfaces used in other systems; and the method of detachment is fast, easy, and it does not harm the cells.

Conductive immunopolymers represent a novel approach to immunoaffinity and cell selection. In one embodiment, conductive immunopolymers are synthesized by electrically inducing polymerization of organic monomers in the presence of antibodies. This process results in the entrapment of monoclonal antibodies into a conductive solid matrix designated as a conductive immunopolymer. None of currently available cell selection devices integrate this type of conductive solid matrix.

Conductive polymers can also be formed using enzyme generated means. In one embodiment, a polymer can be formed using an enzyme generated conducting polyphenol polymer system. Horseradish peroxidase (HRP) can be used to catalyze the polymerization of a stable electroactive phenolic conducting polymer onto the surface of a glass electrode (Alva et al., 1996; the disclosure of which is herein incorporated by reference).

Incorporation of an antibody into enzyme generated polymers allows not only capture and isolation of cell populations, but also, through electrochemical measurements, provides for the monitoring of both binding and release of captured cells. Enzyme generated conductive polymers offer the following advantages as well: (1) it is a one step process; (2) there are no special purification steps; (3) the environment is totally aqueous; (4) the uncharged polymer allows for the design of positively or negatively charged, pH-type titrateable functional groups into the membrane that can assist in cell isolation; and (5) provides for the addition of other enzymes to the system such that the enzyme electrode can act as a potential specific biosensor that can be utilized in the development of monitoring systems for cell binding, release and viability.

The ability to monitor the cell binding to the solid matrix during the selection process has never before been an option. The use of a conductive immunopolymer provides this advantageous capability. The number of cells bound to the conductive polymer can be monitored by measuring the sum of the micro currents induced by each cell when maintained in immediate proximity of the polymer surface via the antibody. In the context of an "on line" separation device, this feedback information on the number of cells selected at any one time increases the efficiency and safety of the selection process since it allows the monitoring of the procedure by a computer or an operator.

The complete and gentle release of matrix bound cells represent another challenge for today's cell selection devices. Most current positive selection procedures yield altered selected cells since antibodies are still bound to their surface. The use of an electric current to induce the release of bound cell from the immunopolymer surface provides a reliable, reproducible and gentle method to harvest unaltered selected cells.

The binding capacity and specificity of the immunopolymer are primarily determined by the concentrations and specificities of the antibodies included in the polymerization mixture. The rapid and efficient selection of rare cells in large cell mixtures requires that cells interact with vast surface areas of immunopolymers. Beads represent an efficient way to present large immunoselective surface areas to a cell mixture, however, such structure is not compatible with the use of the conductive properties of the immunopolymer. Therefore, in a preferred embodiment, the subject invention utilizes polymer structures such as capillaries, spiral sheets, and parallel sheets with large surface areas and consistent conductive properties.

Non-specific binding is a critical factor limiting the specificity of the current cell selection devices. In order to electrostatically minimize non-specific binding, the immunopolymer can be designed to expose a negative net charge at the cell-matrix interface. This negative charge needs to be strong enough to prevent binding of irrelevant cells but weak enough to not interfere with the specific interaction between antibodies and target cells. Such negative charge can be a direct consequence of the polymer chemical structure or induced by a current. The latter possibility offers flexibility since it allows the operator/computer to adjust the net charge of the polymer surface to various samples and selection conditions.

Also, the prospect of a computer controlled device for the "in line" selection of stem cells from whole blood provides a very significant improvement in terms of ease of use, reliability, reproducability and safety. Only a conductive material can allow a direct interface between electronic controls and cell selection device. This direct interface results in a more reliable, cost effective and simpler design.

The subject invention is exemplified herein using certain conductive polymers with specific antibodies. For example, antibodies to CD34 are specifically exemplified herein. However, those skilled in this art, having the benefit of the instant disclosure could readily utilize other conductive polymers and/or antibodies as described herein to effect the desired stem cell purification. For example, anti-CD4 and anti-CD8 antibodies can be used to purify sub-populations of T lymphocytes that express either CD4 or CD8 determinants.

Suitable antibodies for use in the subject invention include monoclonal and polyclonal antibody compositions. Preferably, the antibodies used in the subject invention are monoclonal antibodies. Whole antibodies and antigen binding fragments thereof are contemplated in the present invention. Thus, for example, suitable antigen binding fragments include $Fab_2$, Fab and Fv antibody fragments.

Antibodies can also be incorporated into the conductive polymer by indirect means. For example, receptors that bind the Fc portion of an antibody molecule can be incorporated into the conductive polymer, then selected antibody can be contacted with the Fc receptor incorporated into the polymer. Antibody is then bound by the Fc receptor. Using this method advantageously provides for orienting the antibody on one particular side of the polymer matrix. Protein G, as well as other antibody binding molecules, can be used according to the subject invention.

Other indirect means can be used to attach antibody to the polymer matrix. In an exemplified embodiment, an avidin-related preparation is incorporated into the polymer matrix. Biotin-labeled antibody, either free or pre-bound to target cells, can then be contracted with and bound by the polymer through the interaction of the avidin-biotin complex formed.

Examples of suitable electrically-conducting polymers include polyheteroaromatic polymers, polyacetylenes, polyparaphenylenes, polyphenylenevinylenes and derivatives thereof. Preferred substrates include polyheteroaromatic polymers. The term "polyheteroaromatic polymer," as defined herein, means an aromatic polymer having repeating units which include at least two elements in the aromatic rings of the repeating units.

Although the mechanism is not completely understood, it is believed that suitable polymers are electrically conductive because electrochemical oxidation, for example, causes positively charged regions, or "defects," which allow electrons to move along polymer chains which include such defects, thereby conducting an electrical current. Examples of suitable polyheteroaromatic polymers include alkyl-substituted polythiophenes and polypyrrole. A particularly preferred polyheteroaromatic polymer is polypyrrole.

The polymer substrate is formed by, for example, electrochemical polymerization. In one example of electrochemical polymerization, a polypyrrole film is formed by disposing a graphite-rod cathode and a platinum-plate anode into a monomer solution of distilled pyrrole. An appropriate current density is maintained at a suitable voltage for a sufficient period of time to cause a polypyrrole film to form on the anode.

Figure 1:
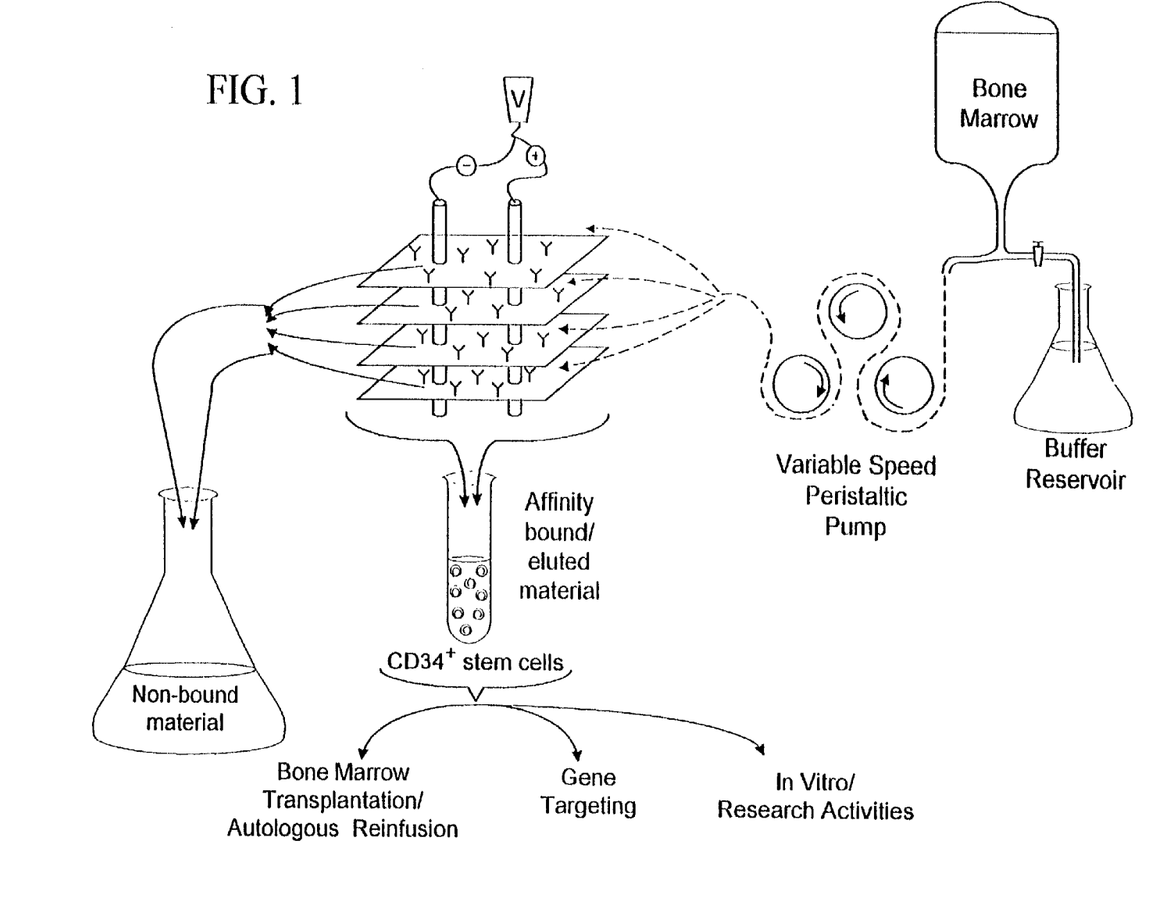
FIG. 1 shows a system according to the subject invention for purifying stem cells.

A further aspect of the subject invention pertains to devices useful in purifying stem cells using the procedures of the subject invention. One system for purifying stem cells is shown in FIG. 1. As shown in this Figure, bone marrow can be passed through membranes of conductive polymers with which antibodies are associated. In a preferred embodiment, the antibodies would be to CD34. As shown in FIG. 1, unbound material passes through the membranes and is discarded or collected for further processing. Cells which are trapped by the polymer/antibody matrix are then released by passing an appropriate current through the polymer. The cells thus released are collected for use in any one of the many applications for purified stem cells.

The subject invention can be used to simultaneously and/or sequentially collect and fractionate various cell types. This can be accomplished by utilizing antibodies with varying specificities for the different cell types. For example, the method of the subject invention can be practiced utilizing antibodies to a various cells associated with the immune system such as T cells, natural killer (NK) cells, B cells, and others. In a specific embodiment, these cells can be removed for a composition simultaneously by using multiple antibodies with differing specificities. These antibodies may be localized in different layers of a multiple layer polymeric matrix. In this embodiment, the current applied to the different layers may be modulated so as to release each type of cell at a separate time thereby facilitating the efficient purification and separation of these cells.

The subject invention can also be used to isolate targets such as virus particles, proteins, polynucleotides, and the like, using molecules incorporated in the polymer matrix that bind to the target moiety. The targeted material is contacted with the polymer and then washed to remove unbound material. Bound material can be released according to the methods of the invention.

Although antibodies are exemplified herein as molecules capable of binding to a target moiety, other types of molecules can also be used with the subject invention. For example, cell adhesion molecules, lectins, ligands, receptors and the like can also be incorporated into a conductive polymer. In addition, polynucleotide molecules can be immobilized in a polymer matrix and used to selectively bind other polynucleotides, or even proteins, depending on the binding specificity and sequence of the polynucleotide.

Following are examples which illustrate procedures for practicing the invention. These examples should not be construed as limiting. All percentages are by weight and all solvent mixture proportions are by volume unless otherwise noted.

EXAMPLE 1

CD34$^+$ Cell Binding as a Function of Polymer Type and Antibody Concentration

It is difficult to obtain human hematopoietic stem cells. Therefore, ML-1 cells, a human non-adherent cell line expressing CD 34, was used to determine the capacity and specificity of the interaction between CD34$^+$ cells and immunopolymers.

ML-1 cells were grown in Iscove's modified Dulbecco's medium (IMDM) supplemented with 10% fetal bovine serum (FBS) and antibiotics (50 U/ml penicillin and 50 U/ml streptomycin). Cells were grown to confluence, then harvested by centrifugation, washed and resuspended at a concentration of $10^5$ cells/ml.

The antibody used to give specificity to the conductive polymer was an anti-CD34 monoclonal antibody (HPCA-1, supplied at 50 µg/ml in phosphate buffered saline with gelatin and 0.1% sodium azide, Becton Dickinson, CA). The antibody was stored at 4° C.

Two types of polymers were prepared. The polymers were prepared as follows:

Polymer 1: Polypyrrole doped with naphthalene sulfonate.

The following solutions were combined into a 50 ml beaker:
  20 ml of a 0.08 M aqueous solution of 2-naphthalene sulfonate (pH 2.0)
  1.5 ml of freshly distilled pyrrole (0.2 M final concentration)
  various masses of anti CD34 antibody (0, 5, 10, and 20 µg).

Polymer 2: Polypyrrole doped with p-toluene sulfonate.

The following solutions were combined into a 50 ml beaker:
  20 ml of a 0.1 M p-toluene sulfonic acid dimethyl ammonium salt
  1.5 ml of freshly distilled pyrrole (0.2 M final concentration)
  various masses of anti CD34 antibody (0, 5, 10, and 20 µg).

For each type of conductive polymer, reagents were added and mixed, then polymerized in a polymerization chamber with an indium tin oxide-coated glass anode and a platinum cathode, under a current of 1.6 V for 30 seconds followed by 1.0 V for 20 minutes. After polymerization, the polypyrrole membranes were removed from the anode, washed with IMDM and transferred into wells of 6-well culture plates containing 3 ml of complete medium each.

CD34$^+$ cells ($10^5$ in 1 ml complete IMDM/well) were added to the polypyrrole membranes and incubated for 1 hour at 37° C. in a non-gassed incubator. Following incubation, the membranes were removed from the cell suspensions, washed, then stained using a modified Wright-Giemsa stain. The membranes were dried and fixed to a glass slide under a quick dry mounting medium and observed under light microscopy for the following parameters: number of bound CD34$^+$ cells, uniformity of binding, and membrane thickness.

Figure 2:
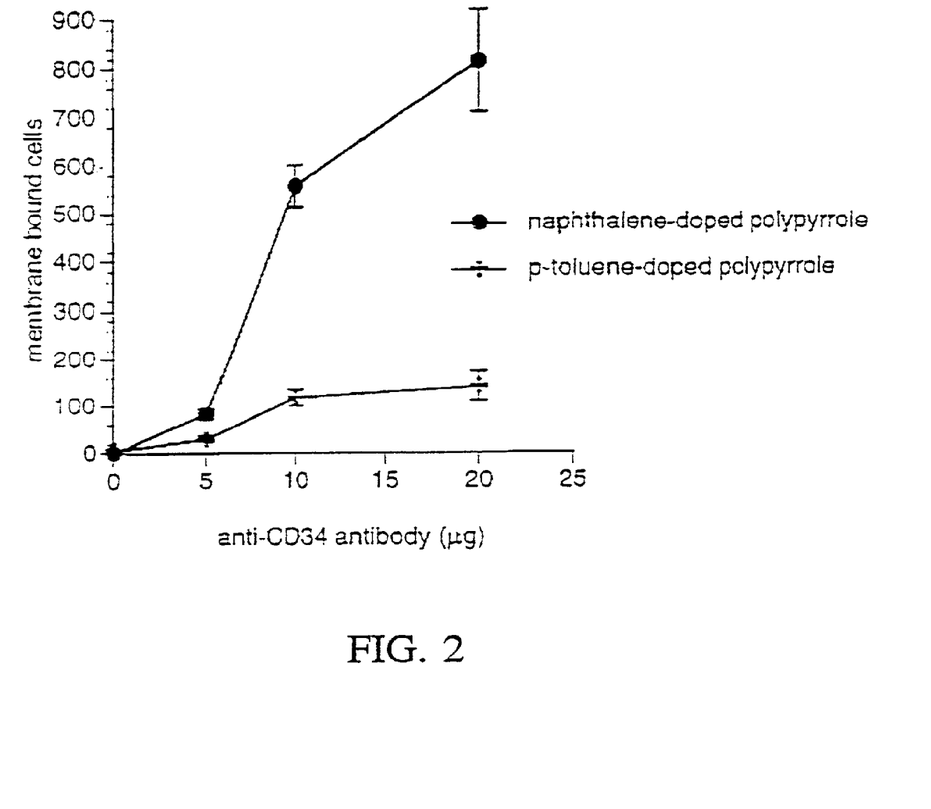
FIG. 2 shows capacity of 2 different types of conductive immunopolymers to bind $CD34^+$ cells as a function of increasing amounts of anti-CD34 antibody present during the polymerization reactions.
Figures 3A, 3B:
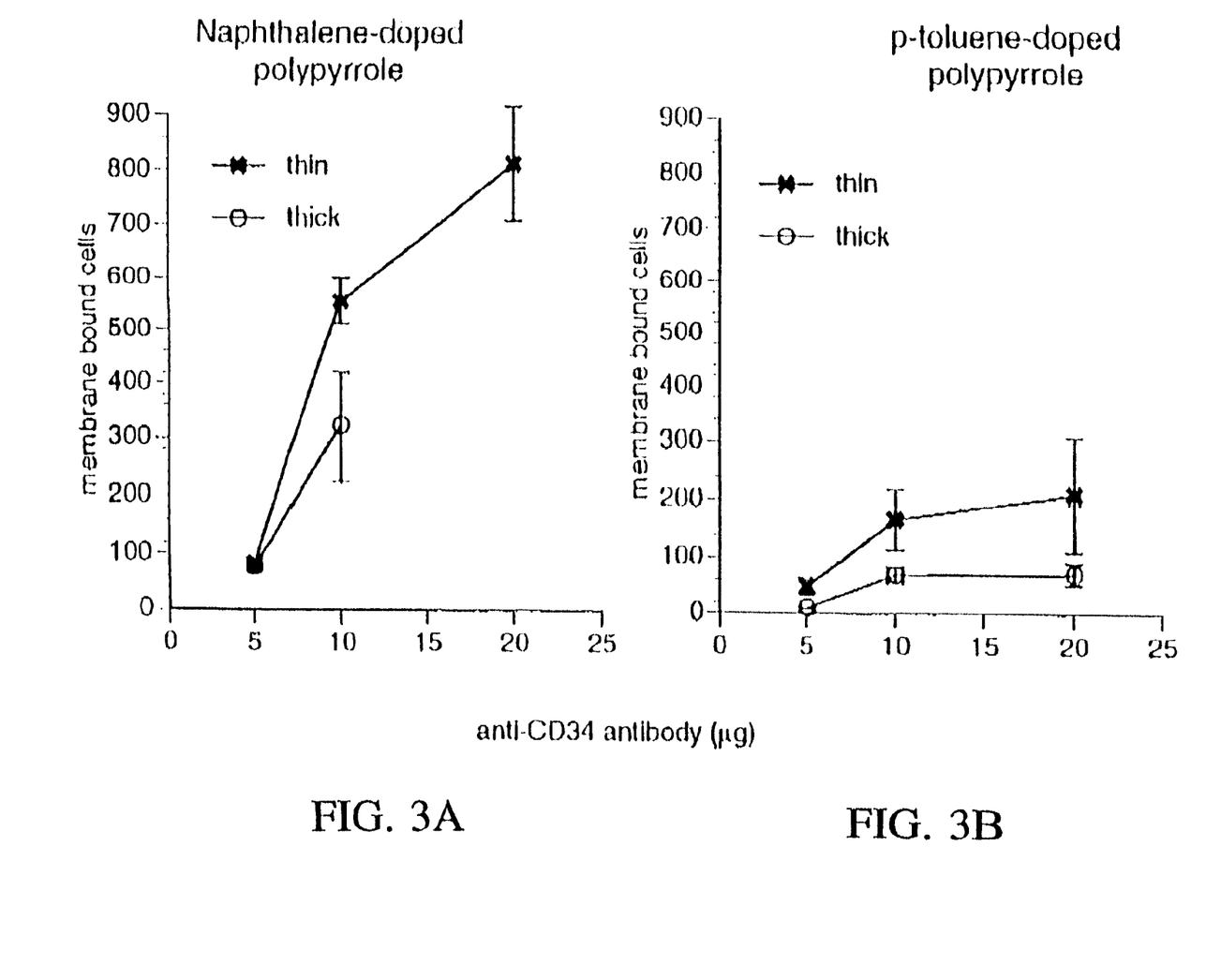
FIG. 3 shows effect of thickness of the membranes on cell binding capacity of the 2 types of conductive immunopolymers.

In these experimental conditions, non specific binding of CD34$^+$ cells to the polymers was insignificant. When anti-CD34 antibody was present during the polymerization reaction, both types of conductive immunopolymers bound CD34+ cells. However, for equal amounts of antibody present, the naphthalene-doped polypyrrole showed a higher binding capacity than the p-toluene-doped polymer (FIG. 2). Thickness of the polypyrrole membranes influenced their binding capacity since more CD34+ cells were bound in the thinner areas of membranes (FIG. 3).

EXAMPLE 2

Effect of Polymerization Time on Cell Binding Capacity

The objective of this experiment was to determine the optimal polymerization time in the presence of antibody to obtain the highest cell binding capacity for the polypyrrole membranes.

ML-1 cells were grown in Iscove's modified Dulbecco's medium (IMDM) supplemented with 10% fetal bovine serum (FBS) and antibiotics (50 U/ml penicillin and 50 U/ml streptomycin). Cells were grown to confluence, then harvested by centrifugation, washed and resuspended at a concentration of $10^5$ cells/ml.

The antibody used to give specificity to the conductive polymer was an anti-CD34 monoclonal antibody (HPCA-1, supplied at 50 µg/ml in phosphate buffered saline with gelatin and 0.1% sodium azide, Becton Dickinson, CA). The antibody was stored at 4° C.

Two types of polymers were prepared. The polymers were prepared as follows:

Polymer 1: Polypyrrole doped with naphthalene sulfonate.

The following solutions were combined into a 50 ml beaker:
  20 ml of a 0.08 M aqueous solution of 2-naphthalene sulfonate (pH 2.0)
  1.5 ml of freshly distilled pyrrole (0.2 M final concentration)
  various masses of anti CD34 antibody (0, 5, 10, and 20 µg).

Polymer 2: Polypyrrole doped with p-toluene sulfonate.

The following solutions were combined into a 50 ml beaker:
  20 ml of a 0.1 M p-toluene sulfonic acid dimethyl ammonium salt
  1.5 ml of freshly distilled pyrrole (0.2 M final concentration)
  various masses of anti CD34 antibody (0, 5, 10, and 20 µg).

For each type of conductive polymer, reagents were added and mixed, then polymerized in a polymerization chamber with an indium tin oxide-coated glass anode and a platinum cathode, under a current of 1.6 V for 30 seconds followed by 1.0 V for 20 minutes.

After polymerization, the polypyrrole membranes were removed from the anode, washed with IMDM and transferred into wells of 6-well culture plates containing 3 ml of complete medium each.

Figure 4:
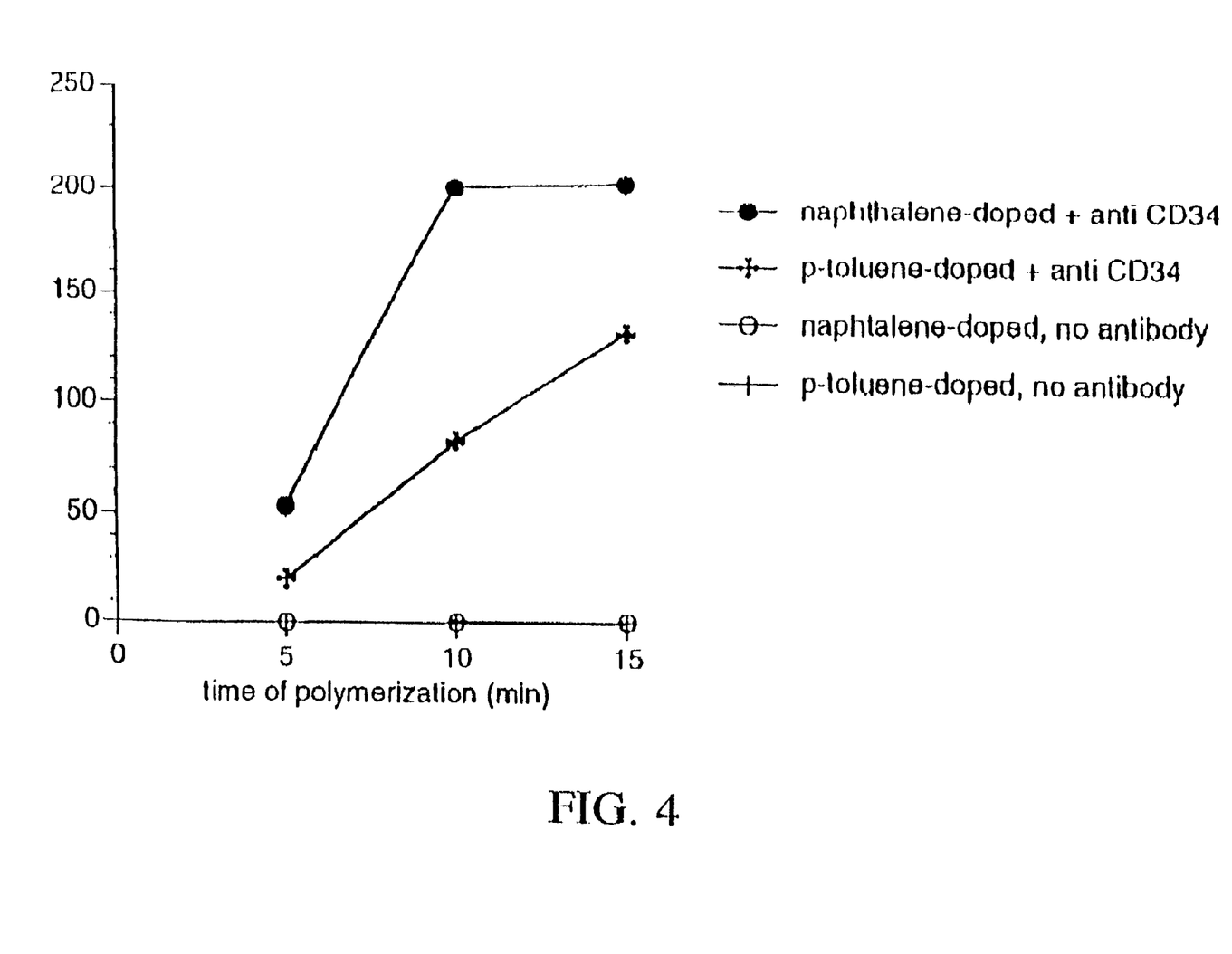
FIG. 4 shows effect of time of polymerization (+ or − anti-CD34 antibody) on the cell binding capacity of the 2 types of polypyrrole polymers.

The cell binding capacity of the polymers increased with polymerization time. The higher cell binding capacity of the naphthalene-doped polypyrrole compared to the p-toluene-doped polypyrrole was already apparent after 5 minutes confirming the result obtained in the first experiment (FIG. 4). The binding capacity of the naphthalene-doped polymer did not increase between 10 and 15 minutes suggesting that polymerization and antibody incorporation were complete in 10 minutes.

EXAMPLE 3

Capacity and Specificity of Binding

NSC1.1 cells, a human non-adherent cell line expressing high levels of the CD 34 antigen, was used to determine the capacity and specificity of interaction between CD34+ cells and the polyphenol polymers. NSC1.1 cells were cultured in Iscove's modified Dulbecco's medium (IMDM) supplemental with 10% fetal bovine serum (FBS) and antibiotics (50 U/ml penicillin and 50 U/ml streptomycin); at 37° C. in an humidified atmosphere of 5% $CO_2$ in air. Cells were harvested by centrifugation (4 min. at 300×g), washed using complete growth medium and resuspended at a concentration of $10^5$ cells/ml in Iscove's complete medium. To determine the specificity of cell binding, a B lymphocyte cell line characterized as CD34− and CD19+ was used. This cell line was derived from a normal bone marrow aspirate. The B cell line was cultured under the same conditions as the NSC1.1 cells. The antibodies selected to test the binding specificity to the polyphenol conducting polymer was an anti-CD34 monoclonal antibody (HPCA-1) and a anti-CD19 antibody (Becton Dickinson Immunocytometry Systems, CA). Both these antibodies were supplied at 50 µg/ml in phosphate buffered saline with gelatin and 0.1% sodium azide.

Studies using anti-CD34 antibodies entrapped in conducting polypyrrole electrode matrices have been successfully carried out. Table 2 demonstrates the binding of CD34+ cells to 2 different polypyrrole matrices containing anti-CD34 antibodies. These results indicate that, in the absence of antibodies in the system, the polypyrrole polymers do not bind CD34+ cells (therefore there is no non-specific binding). Membranes that have antibody (anti-CD34) incorporated into the polymer matrix do capture CD34+ cells (specific binding) and furthermore, the binding capacity of the immunopolymers increases proportionally when the concentration of anti-CD34 antibodies entrapped in the polymers is increased.

TABLE 1

CD34+ cell selection by electrochemically synthesized immunopolymers.
Polymer Matrix/CD34+ Cells Bound[1]

| Antibody Concentration | Naph. Sulfonate Doped PolyPyrrole | p-Toluene Sulfonate Doped PolyPyrrole |
|---|---|---|
| 0 | 0 (±0)[2] | 0 (±0) |
| 5 | 82 (±11) | 48 (±15) |
| 10 | 556 (±44) | 116 (±52) |
| 20 | 814 (±104) | 210 (±99) |

[1]=approximately $10^3$ CD34+ cells were added to a 2 cm² polymer membrane
[2]=S.E. of the mean for 6 replicates

EXAMPLE 4

Specificity of Binding

To test the specificity of interaction between cells and conductive immunopolymers, antibodies with two different specificities (anti-CD19 and anti-CD34) were incorporated into separate membranes. These immunopolymers specific for CD34 or CD19 were tested for their ability to specifically bind to CD34+ or CD19+ cells.

The ML-1 cell line were used as a source CD34+, CD19− cells. Wilkinsons cells, a B-cell lymphoma clinical isolate from a bone marrow aspirate, were used as a source of CD34⁻, CD19⁺ cells. CB-1 cells, a primitive neuro-ectodermal tumor line, were used as source of CD34⁻, CD19⁻ cells. ML-1, Wilkinsons and CB-1 cells were grown in Iscove's modified Dulbecco's medium (IMDM) supplemented with 10% fetal bovine serum (FBS) and antibiotics (50 U/ml penicillin and 50 U/ml streptomycin). Cells were grown to confluence, then harvested by centrifugation, washed and resuspended at a concentration of $10^5$ cells/ml.

The antibodies used were anti-CD34 monoclonal antibody (HPCA-1, supplied at 50 μg/ml in phosphate buffered saline with gelatin and 0.1% sodium azide, Becton Dickinson, CA), and anti-CD19 monoclonal antibody (Becton Dickinson, CA).

A naphthalene-doped polypyrrole was used to assess binding specificity. The following solutions were combined into a 50 ml beaker:

20 ml of a 0.08 M aqueous solution of 2-naphthalene sulfonate (pH 2.0)

1.5 ml of freshly distilled pyrrole (0.2 M final concentration)

various masses of anti CD34 antibody (0, 5, 10, and 20 μg).

Naphthalene and pyrrole were thoroughly mixed for 1 minute, then the magnetic stirrer was switched off and the polymerization was initiated using a current of 1.6 V for 30 seconds followed by 1.0 V for 10 minutes. Polypyrrole membranes containing anti-CD34 or anti-CD 19 or no antibody were prepared. After polymerization, the newly formed membranes were removed from the chamber, washed with IMDM and transferred into wells of 6-well culture plates containing 3 ml of complete medium each.

After incubation with ML-1 or Wilkinsons, or CB-1 cells, the number of membrane-bound cells were determined by light microscopy. Results are summarized in Table 2.

TABLE 2

Cell binding specificity of a naphthalene-doped conductive polymer. Data represent the number (± SE) of cells bound to naphthalene-doped polymers containing different types of antibodies (anti-CD34 or anti-CD19 or none).

| Cell Type | Naphthalene-doped polypyrrole specificity | | |
|---|---|---|---|
| | anti-CD34 | anti-CD19 | none |
| CD34⁺/CD19⁻ (ML-1) | 146 ± 29[1] | 1.5 ± 2. | (−)[2] |
| CD34⁻/CD19⁺ (Wilk.) | (−) | 8.6 ± 1.5 | (−) |
| CD34⁻/CD19⁻ (CB-1) | (−) | (−) | (−) |

[1]=S.E. for the mean of 4 membranes (500 cells added/membrane + 10 μg total antibody)
[2]=(−) no visible cells binding Only cells expressing the CD marker recognized by each antibody type were able to bind the conductive immunopolymers suggesting that the interaction between cells and polymer is specifically mediated through the monoclonal antibodies included in the polymer.

EXAMPLE 5

Specific Selection of Rare CD34⁺ Cells from a Large Excess of CD34⁻ Cells

The objective of this study was to determine the ability of a naphthalene-doped immunopolymer to specifically bind rare CD34⁺ cells in the context of a large excess of CD34⁻ cells.

The ML-1 cell line was used as a source CD34⁺, CD19⁻ cells. CB-1 cells, a primitive neuro-ectodermal tumor line, were used as source of CD34⁻, CD19⁻ cells. ML-1 and CB-1 cells were grown in Iscove's modified Dulbecco's medium (IMDM) supplemented with 10% fetal bovine serum (FBS) and antibiotics (50 U/ml penicillin and 50 U/ml streptomycin). Cells were grown to confluence, then harvested by centrifugation, washed and resuspended at a concentration of $10^5$ cells/ml.

In order to visualize the two different cell populations, the CD34⁺ cells were stained dark blue using a Giemsa stain. The CD34⁻ cells (CB-1) were stained pale pink. Stained cells were enumerated and CD34⁺ cells (ML-1) were seeded into CB-1 cells so that ML-1 cells represent only 10% of all cells in the mixture.

The antibodies used were anti-CD34 monoclonal antibody (HPCA-1, supplied at 50 μg/ml in phosphate buffered saline with gelatin and 0.1% sodium azide, Becton Dickinson, CA).

A naphthalene-doped polypyrrole was used to assess binding specificity. The following solutions were combined into a 50 ml beaker:

20 ml of a 0.08 M aqueous solution of 2-naphthalene sulfonate (pH 2.0)

1.5 ml of freshly distilled pyrrole (0.2 M final concentration)

Various masses of anti CD34 antibody (0, 5, 10, and 20 μg).

Naphthalene and pyrrole were thoroughly mixed for 1 minute, then the antibody was added, and the mixture was stirred for an additional minute. Then, the magnetic stirrer was switched off and the polymerization was initiated using a current of 1.6 V for 30 seconds followed by 1.0 V for 10 minutes. After polymerization, the newly formed membranes were removed from the chamber, washed with IMDM and transferred into wells of 6-well culture plates containing 3 ml of complete medium each.

The cell mixture (90% CB-1+10% ML-1) was applied to the polymerized membranes and incubated for 30 minutes at 37° C. in a non-gassed incubator. Following incubation, the membranes were removed from the cell suspensions, washed 3 times, air dried and fixed to a glass slide under a quick dry mounting medium. The slide-mounted membranes were observed under light microscopy to determine the color (dark blue versus pale pink) and the number of bound cells.

Based on color, the CD34⁺ cells represented 7.6% of all cells. After 30 minutes of incubation, only dark blue cells (CD34⁺) were observed at the surface of the membranes. These results indicate that the naphthalene-doped polypyrrole can be used to select CD34⁺ cells in a cell mixture containing a large excess of irrelevant cells.

EXAMPLE 6

Recovery and Viability of Target Cells

The ability of the subject invention to capture and release a target cell population was demonstrated using a purified CD34⁺ cell population as the starting material. The polymer was prepared with anti-CD34 antibody incorporated therein as described previously.

TABLE 3

Recovery and viability of CD34+ selected cells.

| # of CD34+ cells added | Mean Cell Count (CD34+) 500 | Mean Percent |
|---|---|---|
| CD34+ Cells Bound | 448 ± 14[1] | 90 ± 2 |
| CD34+ Cells Released/Recovered | 378 ± 12 | 84 ± 1 |
| Viability of CD34+ cells Recovered | 362 ± 6 | 96 ± 2 |

[1]S.E. of the mean for 4 membranes
[2]10 µg total antibody was added to the polymer mixture The ability to specifically capture rare cells, such as HSC, from a complex mixture of irrelevant cells (peripheral blood, and/or bone marrow) is an important requirement for efficient cell selection. Non-specific binding is a critical factor limiting the specificity of the current marketed devices. The conducting properties of this type of polymer can be exploited to minimize this phenomenon by modulating the net charge of the immunoaffinity surface in order to prevent non-specific binding while allowing specific antibody-based cell binding. Therefore, the ability of a conductive polymer of the subject invention to be able to capture targeted cells from a complex tissue such as peripheral blood or bone marrow was examined. CD34+ cells were seeded at varying concentrations (10%, 5% and 1%) into freshly isolated peripheral blood leukocytes (PBL) and the mixture applied to an immunopolymer comprising anti-CD34 antibody (10 µg total anti-CD34 antibody). The results from one of those experiments is shown in Table 4. The data shows that a conductive polymer of the present invention is capable of selectively binding to a target cell population (in this study CD34+) and recovering a high percentage of cells with an extremely high degree of purity (see Table 4). These data strongly suggest that the present invention is capable of performing to a high level of accuracy (specific target cell recovery) when applied to a complex cell suspension and can selectively capture stem cells at concentrations equivalent to those found in clinical relevant samples of mobilized peripheral blood (1–5%).

TABLE 4

Selective binding and percent capture of CD34+ cells from peripheral blood leukocytes.
% CD34+ Cells Recovered From PBL (Mean of 6 membranes)

| % CD34+ Cells/PBL | CD34+ Recovered | Purity | Viability |
|---|---|---|---|
| 10% | 83% | 89.2% | 96% |
| 5% | 93% | 93.5% | 95% |
| 1% | 70% | 94.4% | 93% |

A donor bone marrow harvest ranges on average between 700–1000 ml resulting in a total nucleated cell count of approximately $1-2\times10^{10}$. Assuming an average of 1% CD34+ in normal marrow, the total CD34+ count would average $1-2\times10^8$. It is accepted that a minimum of $1\times10^6$ cell/Kg is required for CD34+ cell transplantation. Therefore, a transplant patient with an average weight of 75 Kg required $75\times10^6$ CD34+ cells for a successful transplant. This is compared to $10^8$ Kg total nucleated bone marrow cells that would be required for a similar bone marrow transplant. Thus, the purity (93%–95%) and cell recovery rate (70%–93%) obtained using a conductive immunopolymer according to the present invention is adequate to give the required concentration of cells for transplantation.

EXAMPLE 7

Indirect Entrapment of Anti-CD34 Antibody in the Polymer Via Immobilized NeutrAvidin NEUTRAVIDIN is immobilized in a polyphenol matrix under optimal conditions of accessibility. NEUTRAVIDIN (Pierce, Rockford, Ill.) is a biotin binding protein that lacks both the carbohydrate domain of avidin and the RYD (fibronectin mimic) cell surface receptor binding domain of streptavidin. Both of these domains can lead to significant non-specific cell binding levels.

Either the biotin-anti-CD34 antibody complex can be bound to the immobilized, surface-exposed NEUTRAVIDIN, followed by CD34+ cell binding; or the CD34+ cell population can be pre-mixed with and bound to biotin-anti-CD34 antibody, followed by binding of the biotin-anti-CD34 antibody-CD34+ cell complex to surface immobilized and accessible NEUTRAVIDIN in the polyphenol matrix. With either of these two approaches, a number of biotin derivatives of anti-CD34 antibody can be used. These derivatives are described below. Their advantages are: (1) that they provide relatively mild cleavage chemistries, making possible anti-CD34 antibody; CD34+ cell release; (2) they are long chain derivatives allowing for closer contact between the polyphenol matrix and the bound CD34+ cell; and (3) they allow for better orientation of the anti-CD34 antibody (antigen-binding region oriented outward) in the selection system matrix.

S—S— Cleavable Biotins

NHS—SS-Biotin and Biotin-HPDP are two reagents (Pierce, Rockford, Ill.) containing —S—S— bonds. Both are long chain length reagents (24.3 and 29.2 Å respectively). NHS—SS-Biotin will react with amine groups on the antibody. This biotinylated anti-CD34 antibody species interacts with NEUTRAVIDIN in the normal way, but the —S—S— bond can be chemically cleaved under reducing conditions (50 mM DTT or 100 mM β-mercaptoethanol) releasing the antibody bound to the CD34+ cell. Biotin-HPDP is a unique reagent that can react with sulfhydryls. If the CD34 antibody is first reduced under mild conditions with mercaptoethylamine-CD1 in EDTA, the antibody will be cleaved at the level of disulfide bonds between the two heavy chains generating —SH groups on each heavy chain. This mild reduction treatment will retain the antigen-specific binding capacity of the antibody. At this point, the Biotin-HPDP may be reacted against these —SH groups in the hinge region of the molecule. The reaction is complete within 90 minutes in a range of buffers pH 6–9. Following binding of the antibody to CD34+ cells, this complex will be added to the polyphenol matrix. Once bound to the polymer, the biotin can be cleaved and removed with either 100 mM β-mercaptoethanol or 50 mM DTT (Pierce, Rockford, Ill.) to release the cells.

NHS Iminobiotin and Iminobiotin Hydrazide

These derivatives of biotin (the guanidino analog) have the interesting and useful properties that at neutral to higher pH (maximum binding level above pH 9) they bind normally to the NEUTRAVIDIN binding site. When the pH is lowered below pH 6, their affinity is gradually reduced, and at pH units close to 4, it is totally dissociated. Alternately, the complex can be completely dissociated at any pH by competition with 1 mM biotin for 15 min. (Zeheb et al., 1983). Therefore, in these studies, the anti-CD34 antibody will be derivatized either at a primary amine with NHS Iminobiotin under the conditions described by the supplier (Pierce, Rockford, Ill.) or at a sialic acid residue in the carbohydrate moiety reacted first with 1 mM $NaIO_4$ (at 0° C.) to form the aldehyde, followed by reaction with Iminobiotin hydrazide (BioAffinity Systems, Inc.) To form the hydrazone stable from pH 2–10. This derivative should result in an anti-CD34 antibody with its antigen binding site oriented outward from the matrix immobilized NEUTRAVIDIN, thus increasing the probability of $CD34^+$ cells binding the anti-CD34 antibody. Conversely, when the derivatized antibody is bound to $CD34^+$ cells first, there will be a greater probability of the Iminobiotin moiety, (oriented near the Fc portion of the antibody molecule) binding preferentially to the polyphenol matrix immobilized, NEUTRAVIDIN. Biotin LC-Hydrazide (Pierce, Rockford, Ill.), a commercially available long chain (24.7 Å) biotin reagent can be used as a substitute for the biotin derivative mentioned above. In all cases, antibodies have been shown to retain full immunological activity following this biotinylation, since the derivatization of carbohydrate resides in the Fc portion of the antibody molecule, distal to the antigen binding site. To obtain strong binding of the Iminobiotin moiety to immobilized NEUTRAVIDIN, the pH will be maintained at pH 8.5 or above.

EXAMPLE 8

Monitoring Systems to Assess Maximum Cell Binding/Release, and the Physiologic State of Bound Cells Exemplified herein are two classes of electrochemical measurements which can be performed to monitor cell binding, release and viability. The first method involves monitoring of change in electrochemical impedance or the related electrochemical parameters (Resistance, capacitance). When cells bind to the conducting immunopolymer via the antibodies, the dielectric constant thickness of the dielectric layer, can change in the vicinity of the electrode surface. At a constant frequency (usually 1–10 Khz), a gradual increase of the impedance could be detected after addition and binding of the cells. The magnitude of the change is typically proportional to the number of bound cells. Kinetics of the cell binding will be followed by continuous monitoring of the impedance. Small platinum or gold interdigitated "comb" electrodes can be used. Impedance can be monitored using a potentiostat coupled with a lock-in amplifier controlled with a computer through an IEEE-488 interface driven by electrochemical impedance software. Preferably, the polymer film is kept very thin ($\leq 100$ Å) to ensure adequate sensitivity to detect cell binding.

A second monitoring system is the enzyme-linked amperometric immunoassays. The microcurrent produced by entrapped reporter enzymes (HRP and glucose oxidase-(GOx)) will sense glucose. This sensing is carried out experimentally by coupling the enzymes HRP and GOx as shown in FIG. 5.

Figure 5:
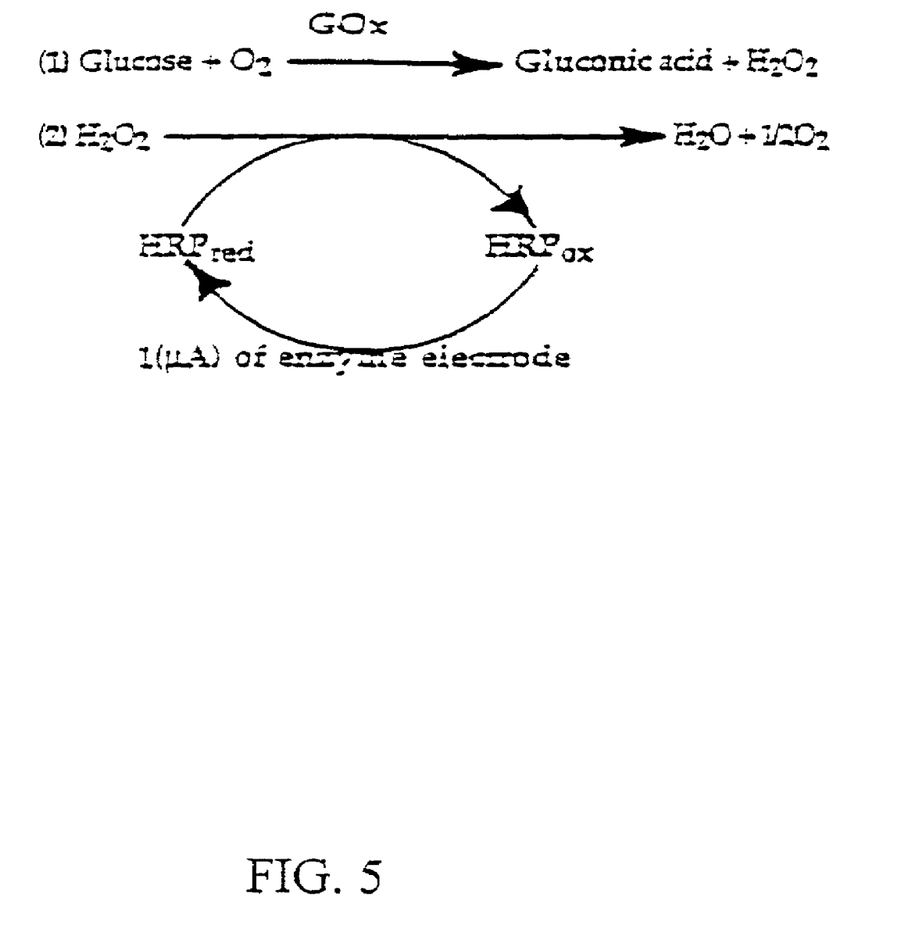
FIG. 5 shows a reaction diagram illustrating the coupling of the enzymes HRP and GOx.

Glucose is reflected as a microcurrent, 1 ($\mu A$), necessary to regenerate the HRP enzyme following cycling through the two-step reaction sequence (FIG. 5). For calibration experiments, different concentrations of glucose can be added to the solution without cells, the current reflecting the production of $H_2O_2$ at a controlled potential $-0.05$ V wrt Ag/AgCl (previously shown to be a safe potential for cells), measured to establish a calibration curve. The current will change as the cells bind due to either the local consumption of glucose or the prevention of it diffusing into the enzyme immobilized electrode by the bound cell. Thus, the change in current will also be capable of calibration and conversion into the number of bound cells. Dynamic curves of current Vs time can be investigated as a function of the adsorption/desorption of $CD34^+$ stem cells seeded at varying concentrations into PBL.

Not only does the latter monitoring system allow for the detection of bound cells and their subsequent release but their viability is also assessable through the glucose measurements. Viable cells possess basal metabolic rates which are capable of calibration by this system. Also, by utilizing other oxidase enzymes, in combination with HRP, other substrate may be assayed that also reflect cell viability.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCE

Alva, K. S., K. A. Marx, L. A. Samuelson (1996) *S.P.I.E.*, 2716:152.

Bender et al. (1991) *Blood*, June, 77:2591–2596.

Berenson, R. J., W. J. Bensinger, R. S. Hill (1991) *Blood*, 77:1717.

de Wynter, E. A., L. H. Coutinho, X. Pei (1995) *Stem Cells*, 13:524.

Zeheb, R., V. Chang, and Orr Ga (1983) *Anal. Biochem.*, 129:156.

U.S. Pat. No. 4,714,680.

What is claimed is:

1. A conductive immunopolymer matrix comprising:
   a) a first immunopolymer layer comprising a polyheteroaromatic polymer and an Fc receptor entrapped within said polymer, wherein a first antibody is bound to said Fc receptor in said first polymer; and
   b) a second immunopolymer layer comprising a polyheteroaromatic polymer and an Fc receptor entrapped within said polymer, wherein a second antibody is bound to said Fc receptor in said second polymer and said second antibody binds to a determinant or antigen that said first antibody does not bind; and
   wherein said first and second immunopolymer layers further comprise a cell monitoring system, wherein said cell monitoring system comprises horseradish peroxidase and glucose oxidase entrapped within said first and second immunopolymers.

2. The conductive immunopolymer matrix according to claim 1, wherein said antibody bound to said Fc receptor of said first immunopolymer layer binds to a CD3, CD4, CD7, CD8, CD10, CD11, CD14, CD19, CD20, or CD33 determinant.

3. The conductive immunopolymer matrix according to claim 1, wherein said antibody bound to said Fc receptor of said second iminunopolymer layer binds to a CD34 determinant.

4. The conductive immunopolymer matrix a according to claim 1, wherein said polyheteroaromatic polymer is an alkyl substituted polythiophene or a polypyrrole.

5. The conductive immunopolymer matrix a according to claim 1, wherein said polyheteroaromatic polymer is a naphthalene sulfonate-doped polypyrole or a p-toluene sulfanate-doped polypyrrole.

6. The conductive immunopolymer matrix according to claim 1, wherein said polyheteroaromatic polymer has a net negative charge at the surface of said polymer.

7. The conductive immunopolymer matrix according to claim 1, wherein said conductive immunopolymer matrix is provided in a capillary, spiral sheet, or parallel sheet.

8. The conductive immunopolymer matrix according to claim 1, wherein said first and second immunopolymer layers are sequentially oriented with respect to each other.

9. A conductive immunopolymer matrix comprising:
   a) a first immunopolymer layer comprising a polyphenol polymer and an Fc receptor entrapped within said polymer, wherein a first antibody is bound to said Fc receptor in said first polymer; and
   b) a second immunopolymer layer comprising a polyphenol polymer and an Fc receptor entrapped within said polymer, wherein a second antibody is bound to said Fc receptor in said second polymer and said second antibody binds to a determinant or antigen that said first antibody does not bind; and
   wherein said first and second immunopolymer layers further comprise a cell monitoring system, wherein said cell monitoring system comprises horseradish peroxidase and glucose oxidase entrapped within said first and second immunopolymers.

10. The conductive immunopolymer matrix according to claim 9, wherein said antibody bound to said Fc receptor of said first immunopolymer layer binds to a CD3, CD4, CD7, CD8, CD10, CD11b, CD14, CD19, CD20, or CD33 determinant.

11. The conductive immunopolymer matrix according to claim 9, wherein said antibody bound to said Fc receptor of said second immunopolymer layer binds to a CD34 determinant.

12. The conductive immunopolymer matrix according to claim 9, wherein said polyphenol polymer has a net negative charge at the surface of said polymer.

13. The conductive immunopolymer matrix according to claim 9, wherein said conductive immunopolymer matrix is provided in a capillary, spiral sheet, or parallel sheet.

14. The conductive immunopolymer matrix according to claim 9, wherein said first and second immunopolymer layers are sequentially oriented with respect to each other.

15. A conductive immunopolymer matrix comprising a polymer and a molecule having binding specificity for a target molecule, wherein said polymer comprises a polyphenol polymer, and wherein said molecule having binding specificity for a target molecule is an Fc receptor and is entrapped within said polymer.

16. The conductive immunopolymer matrix according to claim 15, wherein an antibody is bound to said Fc receptor.

17. The conductive immunopolymer matrix according to claim 16, wherein said antibody binds to a CD34 determinant.

18. The conductive immunopolymer matrix according to claim 16, wherein said antibody binds to a CD3, CD4, CD7, CD8, CD10, CD11b, CD14, CD19, CD20, or CD33 determinant.

19. The conductive immunopolymer matrix according to claim 15, wherein said polyphenol polymer has a net negative charge at the surface of said polymer.

20. The conductive immunopolymer matrix according to claim 15, wherein said conductive immunopolymer matrix is provided in a capillary, spiral sheet, or parallel sheet.

21. The conductive immunopolymer matrix according to claim 15, wherein said conductive immunopolymer matrix further comprises a cell monitoring system, wherein said cell monitoring system comprises horseradish peroxidase and glucose oxidase entrapped within said polymer.

22. The conductive immunopolymer matrix according to claim 15, wherein said conductive immunopolymer matrix comprises multiple layers of said polymer, and wherein a different antibody is bound to said Fc receptor in each of said layers.

* * * * *

UNITED STATES PATENT AND TRADEMARK OFFICE
CERTIFICATE OF CORRECTION

PATENT NO. : 7,015,034 B2
APPLICATION NO. : 09/981639
DATED : March 21, 2006
INVENTOR(S) : Michael J.P. Lawman and Patricia Lawman It is certified that error appears in the above-identified patent and that said Letters Patent is hereby corrected as shown below:

Column 11,
Line 28, "anti-CD 19" should read -- anti-CD19 --.

Column 16,
Line 52, "CD11" should read -- CD11b --.

Column 16,
Line 56, "iminunopolymer" should read -- immunopolymer --.

Column 16,
Line 58, "matrix a according to" should read -- matrix according to --.

Column 16,
Line 61, "matrix a according to" should read -- matrix according to --.

Signed and Sealed this

Fifteenth Day of August, 2006

JON W. DUDAS
*Director of the United States Patent and Trademark Office*